United States Patent [19]

Angeli

[11] Patent Number: 5,593,447
[45] Date of Patent: Jan. 14, 1997

[54] MINIMAL CONTACT PROSTHESIS

[76] Inventor: José A. Angeli, R. Francisco Luiz de Souza Jr. P.3 C-12, Agua Branca - São Paulo-S.P., Brazil

[21] Appl. No.: 522,185

[22] Filed: Aug. 31, 1995

[30] Foreign Application Priority Data

Aug. 25, 1995 [GB] United Kingdom .................... 9517492

[51] Int. Cl.⁶ ...................................................... A61F 2/30
[52] U.S. Cl. ................................................ 623/18; 623/23
[58] Field of Search .................................. 623/18, 19, 20, 623/21, 22, 23

[56] References Cited

U.S. PATENT DOCUMENTS

| 4,221,623 | 9/1980 | Heissler et al. ............................ 623/23 |
| 5,308,412 | 5/1994 | Shetty et al. .............................. 623/23 |
| 5,383,936 | 1/1995 | Kubein-Meesenburg et al. ........ 623/18 |

OTHER PUBLICATIONS

"Campbell's Operative Orthopaedics" Edited by A. H. Crenshaw, vol. Two, Seventh Edition, 1987, pp. 1213–1266.

Primary Examiner—Randy C. Shay
Attorney, Agent, or Firm—Jordan and Hamburg

[57] ABSTRACT

A prosthetic device has first and second components engaging one another in a manner providing for minimal contact bearing surface area to reduce torque during relative motion of said first and second components. In an embodiment of the invention, the first component is an acetabular component and the second component is a femoral component, each adapted for implantation in respective bone structures. The acetabular component has a conical cavity with a circumferential recess and an apex area functional as a primary load bearing surface. The second component is a femoral component with a tapered portion ending in a femoral vertex. In operation, the femoral vertex engages the apex area permitting the femoral component to pivot through a range of normal cooperative motion of the femur and iliac bones.

9 Claims, 6 Drawing Sheets

5,593,447

MINIMAL CONTACT PROSTHESIS

BACKGROUND OF THE INVENTION

The present invention relates to a minimal contact prosthesis and particularly to such a prosthesis to be utilized in arthroplasty, for example hip arthroplasty. Research in arthroplasty has focused on the hip but is equally significant in other joints such as the knee, ankle, shoulder and elbow.

There have been many advances in providing and fixing replacement joints. Among the more important are the discovery of cold-curing acrylic cements for fixation of the components in a prepared bone cavity and the provision of low frictional torque components.

Earlier prostheses for the proximal part of the femur were made of metal and were used to replace the femoral head in fractures, copying as exactly as possible the shape and the size of the proximal part of the femur in order to fit into a corresponding acetabular cavity.

SUMMARY OF THE INVENTION

These early attempts at hip replacement were not particularly successful; the most striking problem being the wear of the acetabular roof in the iliac bone. An obvious solution to this wear was to replace in metal that which was previously provided in bone. A good example of this is the MacKee-Farrar Prosthesis which comprised a metal femoral part and a metal acetabular part, but new problems appeared.

The contact surface was too big and the friction produced between the different components were so high that a significant torque was generated which led to the loosening of the prostheses at the bone/cement interface.

One of the other consequences of the utilisation of joints of this type was that abrasion between the two metallic surfaces released particles of debris which on contact with adjacent cellular material produced an intense immune reaction referred to as metallosis.

Accordingly the Charnley prostheses was developed and is still used today. The Charnley prostheses comprises a relatively small ball portion supported on a femoral insert which cooperates with a corresponding acetabular socket formed of ultrahigh molecular weight polyethylene.

This prostheses has a probable life of about ten years before inevitably friction between the femoral and acetabular parts causes loosening of the components in the bone cavities often at the bone cement interface, which leads eventually to a requirement of a new joint repair. In part, this is also caused by the production of polyethylene debris which produces an adverse immune reaction.

The essential reason for loosening arises because of the frictional torque forces which are produced when the loaded hip moves through an arc. This is in part a function of the frictional forces due to the length of the lever arm that is a function of the radius of the spherical head since the longer the radius the greater the turning moment. This frictional force is transmitted to the acetabular cavity and the femoral component interengaged therewith and thence to the cement/ bone interface. The torque force will eventually cause a reabsorption of the bone, and so loosen the acetabular component.

This problem is exacerbated because the ultra high molecular weight polyethylene tends to wear with time and hence there is a decrease in the low friction qualities of the acetabular cavity leading to an increase in friction.

This invention addresses the above problems and has its genesis in the realization that the problem of the generation of friction between the acetabular cavity and the femoral component could be much reduced if the cooperating load bearing surfaces were reduced to a minimum so that the femoral or second component could change the pattern of the movement between sliding surfaces to a pivotal movement. This is shown in FIG. 8 below. In this figure (A) shows acetabular component 30 in operative engagement with a second or femoral component 31 to create an interface 32. Wear takes place over the whole area of the interface 32 generating debris which will cause an immune reaction.

As shown in FIG. 8B, the acetabular component 40 is provided with a cavity 41 and the bearing surface 43. This bearing surface 43 cooperates in use in this case with a vertex 44 of a second component 42. It will be seen that the second component can move arcuately without generating significant friction or debris.

According to the present invention therefore there is provided a prosthetic or arthroplastic device comprising an acetabular component adapted to be affixed in a prepared cavity in an adjacent cooperating bone, and a second component operatively engaging a cooperating surface in the acetabular component;

The invention being characterized in that both components are provided with respective engagement surfaces whereby the second component comprises a minimal contact bearing surface which is significantly smaller than that of the corresponding acetabular component, whereby load is normally transferred from the acetabular component to the second component, said minimal bearing surface being in contact with a corresponding bearing surface portion in the acetabular component.

The term "acetabular component" relates in addition to its normal designation of a component for positioning in the iliac bone to components which are positioned in similar fashion in the lower end of the tibia (for the ankle); the lower end of the femur (for the knee); in the scapula (for the shoulder); and at the lower end of the humerus (for the elbow).

The second component therefore may be, in addition to a femoral component, a component especially adapted to be positioned in a cavity in a corresponding bone. Preferably the second component is a femoral component adapted to be positioned in a cooperating cavity in the femur, but plainly the second component may be adapted as suggested above for interengagement with other bone sites.

The small or minimal bearing surface of the second component is preferably a vertex of a cone, but depending on the strength of the material chosen, it may be a small sphere so long as the shaft of the second or femoral component is free to movable arcuately, or at least generally linearly.

In a particularly preferred embodiment, the second component subtends an angle more acute than that of the cavity of the acetabular component, with its bearing extremity being a vertex or a very small sphere.

The femoral vertex should not be too sharp at its point to avoid breakage and is best chamfered or formed as a small sphere to provide a substantial load bearing surface. Because the femoral vertex subtends a smaller angle than the acetabular component, the operative portion of the femoral vertex can freely rotate relative to the acetabular component through a wide arc with load transfer still occurring solely through the femoral vertex.

The acetabular component may be formed with a contact surface with a relatively divergent conal shape which terminates in a circumferential slot or recess adapted to entrap the femoral vertex if it should, in abnormal conditions such as the fall of a patient, become unseated from the corresponding acetabular vertex and slide across the surface of the acetabular cone.

It will be appreciated that in use, the femoral and acetabular components are held in tension by musculature and that in normal conditions, the femoral vertex will not separate from the acetabular vertex by a significant amount even when load is removed from the acetabular component as when for example, the patient transfers his weight to the other leg.

The above arrangement prevents insofar as is possible the femoral vertex escaping from the acetabular component during falls etc. This arrangement may be replaced or supplemented by providing that the femoral component is formed with a cone portion terminating remote from the vertex in a flanged portion.

In a particular embodiment, the circumference of the acetabular component is provided with a dentate or saw toothed circumferential edge for cooperation with a second component comprising elements of a cooperating configuration for interengagement therewith. This prevents undesired disengagement of the second component with the acetabular component.

Preferably the distance between the femoral vertex and the flanged portion is slightly greater than the distance between the internal acetabular vertex and the circumferential rim of the acetabular cavity. This provides a normal limit to arcuate movement of the second component relative to the acetabular bone in use but will permit exceptional permissive flexion of the joint if necessary.

If in exceptional circumstances, the femoral flange and the outer circumference of the acetabular component come out of interengagement, because the two components are held by musculature in tension, the femoral vertex will locate in the opposite portion of the circumferential recess so that the femur and the acetabular cavity may be readily restored to their correct inter relation once again.

The components are most preferably formed of a very hard stainless cobalt/chromium alloy. The acetabular component is generally of a shell-like configuration. The outer circumferential surface of the acetabular component is preferably disposed superior to the lower most circumferential surface thereof thereby to provide an overhang in use which reduces the chance of bone overgrowth across the lower circumferential surface which might interfere with the cooperation of the flanged part of the femoral component with the acetabular circumference.

The shell-like external upper surface of the acetabular component may be provided with a convolute surface to allow a suitable cement to firmly affix the said component to a prepared cavity in the iliac or other bone. This convolute surface may be formed by a plurality of concentric channels, by a plurality of small protuberances across its surface, or by other ribs or surface roughening. The acetabular component may also be affixed by screw placement to permit bone ingrowth in a biological fixation.

The tip of the femoral component comprising the femoral vertex, may be made integral with the femoral shaft or may form part of a tip component which interfits therewith.

In a preferred embodiment, the angle formed between the femoral shaft and the femoral tip component may be adjusted by selecting either one of a selection of suitable femoral shafts and/or its length. The length of the tip can be adjusted by altering its position relative to the shaft.

It will be appreciated that the acetabular and second components need to be specially shaped to be suited to their eventual use.

The invention will now be described, by way of illustration only with reference to the accompanying drawings.

DETAILED DESCRIPTION OF THE INVENTION

Figure 1:
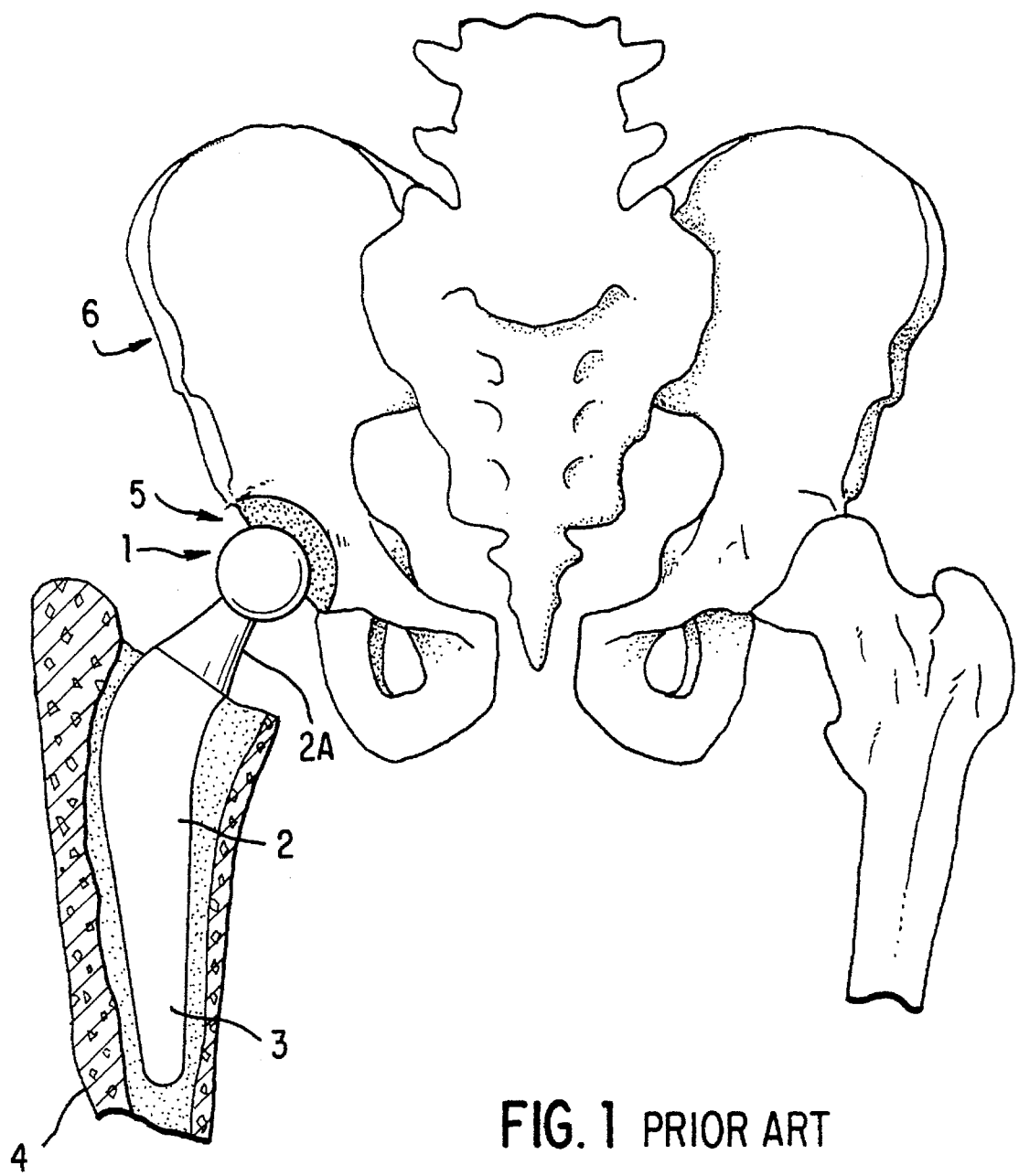
FIG. 1 shows a vertical skeletal view of a prior art arrangement of the prior art in part section.
Figure 2:
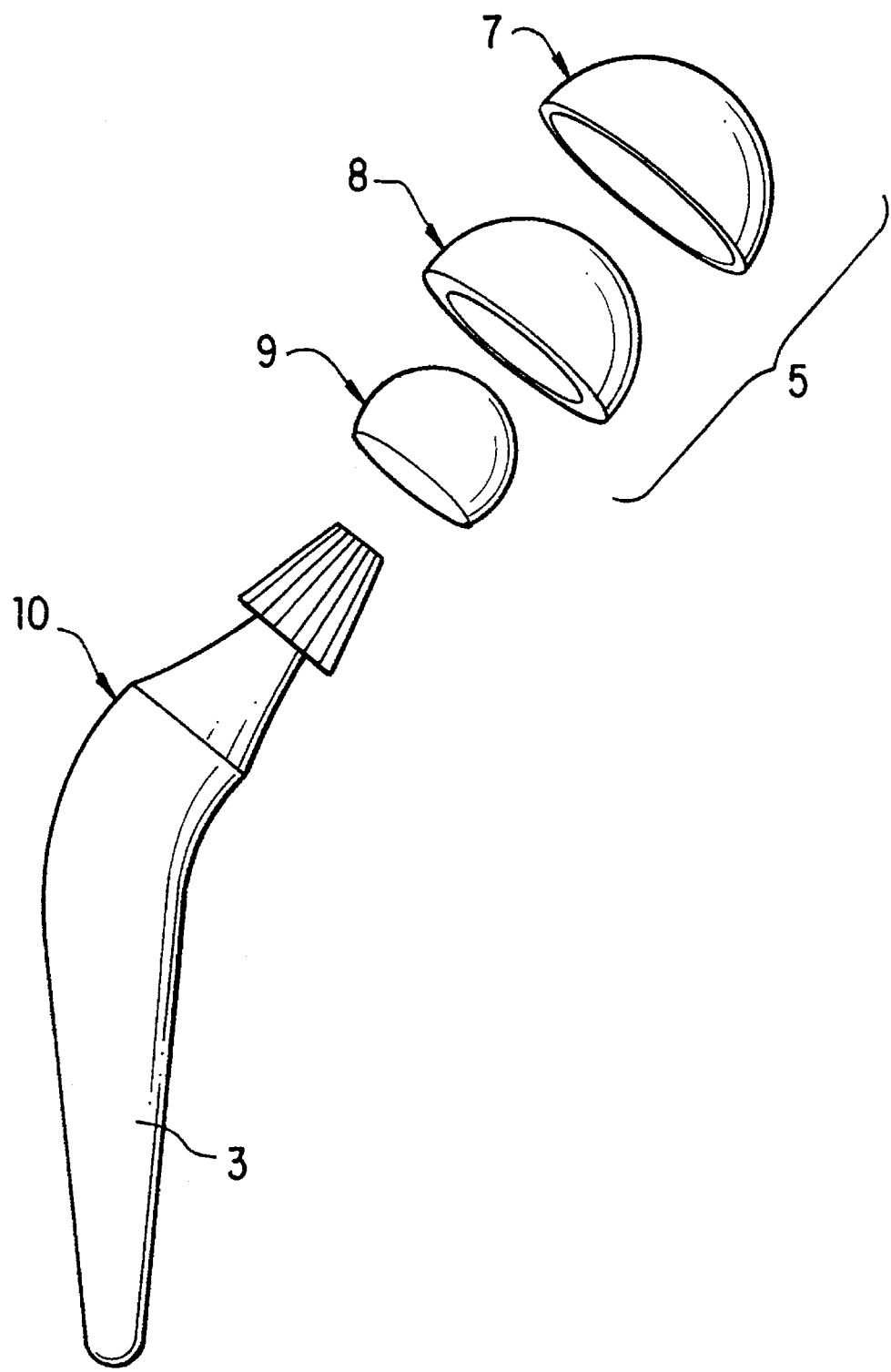
FIG. 2 shows an exploded view of the femoral and acetabular portions utilised in the arrangement of FIG. 1.

With reference particularly to the prior art arrangement of FIG. 1, this shows a standard Charnley arrangement which, with reference to FIG. 2, shows a femoral stem 2 which is provided over its lower portion with a surface 10 which allows of easy cementing to secure the same in a femoral cavity.

The femoral stem 2 terminates in a frusto-cone 2A which in turn interengages in a spherical head (ball) 9 in accordance with known practice.

The metallic shell of an acetabular component in the form of a socket 7 is provided for interengagement with a cooperating cavity member 8 which provides a close cooperative fit with the spherical head 9 in use.

With reference to FIG. 1 it will be seen that the spherical head 5 formed of the components 7 and 8 is located in a iliac cavity by means of a suitable acrylic cement. The femur 4 accommodates therein an acrylic cement 3 which secures a femoral stem 2 to the bone femoral bone 4 in a femoral cavity 4A. It will be appreciated that the spherical head 9 can rotate relative to the cavity member 8 and this allows the femur and hence the leg to rotate through an arc relative to the iliac bone 6.

As previously discussed, this arrangement gives rise to loosening of the acetabular component relative to the iliac bone 6 due essentially to an increase in torque because in part, the ultrahigh molecular weight socket within the acetabular cavity becomes progressively worn. The debris from this can result in an immune reaction which would normally be associated with any loosening that leads to pain.

Figure 3B:
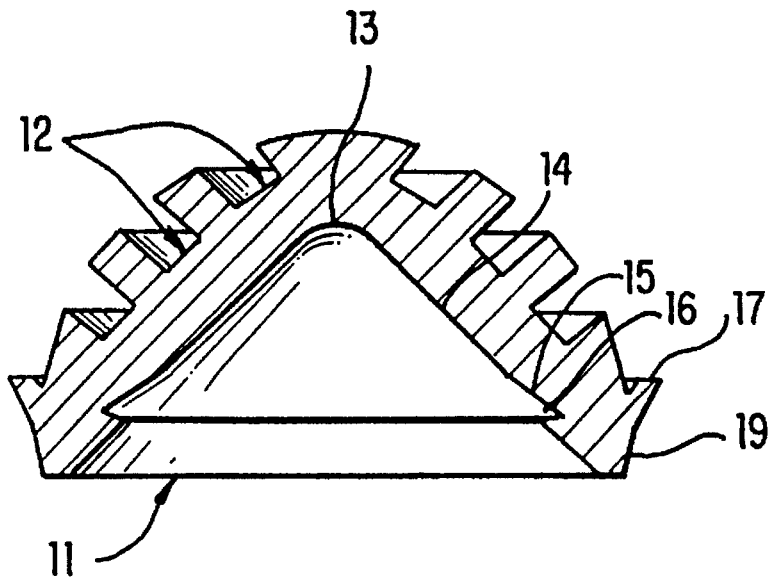
FIG. 3B shows a transverse cross-section along the line "A—A" of the FIG. 3A.
Figure 3A:
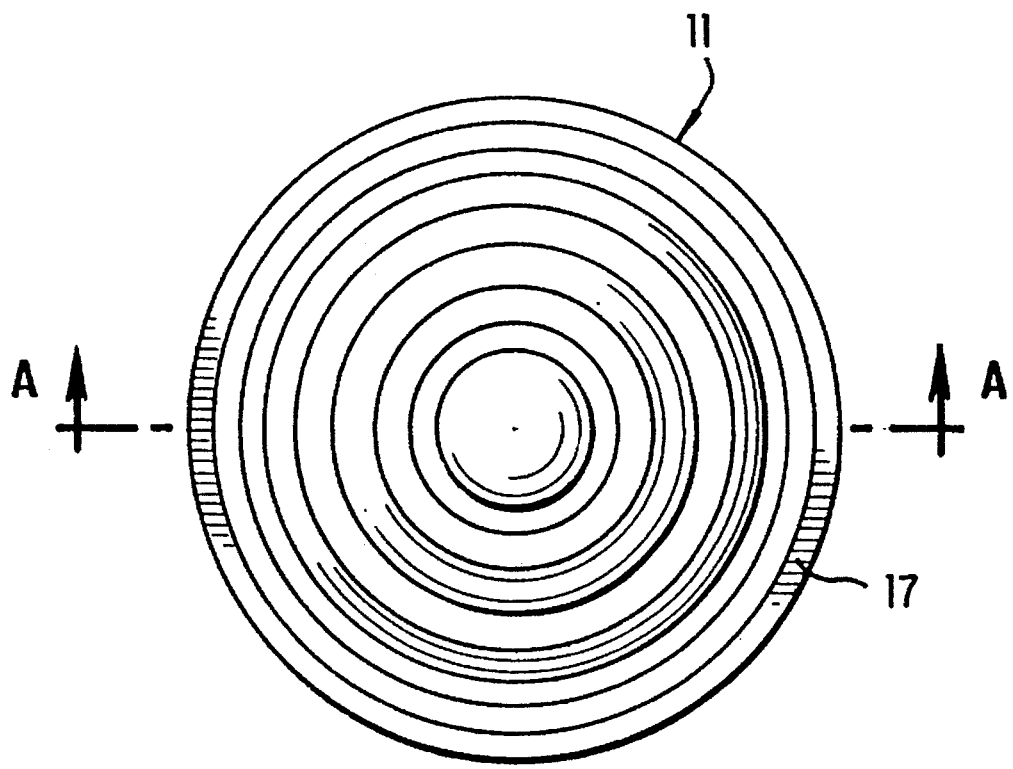
FIG. 3A shows a plan view from above of an acetabular portion.

In order to overcome this, the invention provides an inventive prosthetic shell 11 seen best in plan view in FIG. 3A and in transverse section in FIG. 3B.

With reference to FIG. 3A, the shell comprises in turn a plurality of circumferentially extending channels 12 to allow for substantial fixation to the bone by means of a suitable acrylic cement.

In FIG. 3B, there is shown the acetabular contact point 13 which represents the apex or vertex of a cone shaped cavity 14 which extends at an angle of about 110° (in this case) to define an obtuse angled acetabular cone. This angular divergence is increased towards the circumferentially outer portions 15 of the cone-shaped cavity 14 to define in part an acetabular circumferential recess 16 for purposes to be elucidated below.

With reference again to the external portions of the acetabular component, it will be observed that the acetabular component is provided with an acetabular circumferential flange 17 which extends beyond circumferential portion 19 to form an overhang essentially so that bone overgrowth tends to terminate at or about the flange 17 and does not readily impinge upon the overhanging portion 19. Further, the acrylic cement is pressurized during insertion of the device by the surgeon.

Figure 4:
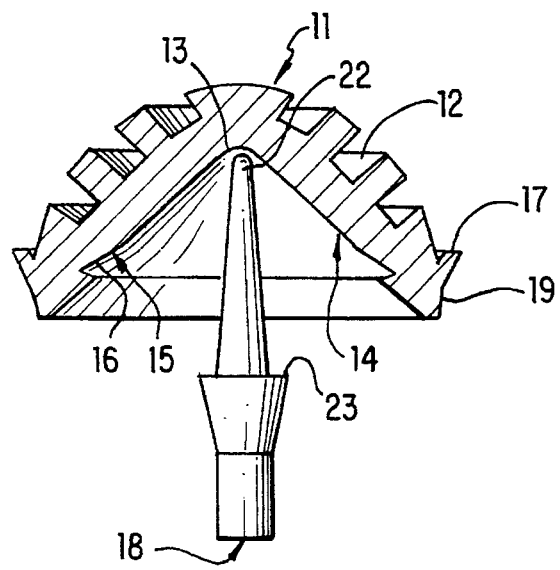
FIGS. 4, 5 and 6 show in part transverse cross-section the arrangement of the invention in various positions.

With reference to FIG. 4, the normal arrangement of the component is shown. In this the acetabular component as shown in FIG. 3 is provided with a femoral component 18 for operative cooperation therewith. The femoral component 18 which comprises a femoral vertex 22 for cooperation with the acetabular vertex (contact point) 13, a femoral flange 23 extending normal to the axis of the femoral component 18; the femoral component 18 and the acetabular component 11 being held in tension by means of connective muscular tissue.

Figure 6:
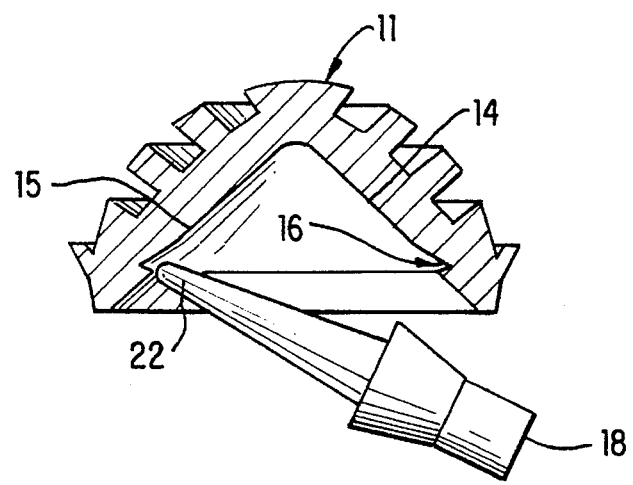

In exceptional circumstances as shown in FIG. 6 for example, the vertex 22 may during a fall, for example, slide down the cavity 14 and nestle in the recess 16 from which, bearing in mind that the femoral component is under musculative tension, the tip 22 will be retained. Accordingly, with the leg reorientated into its proper position, the arrangement of FIG. 4 will be readily restored.

Alternatively, in another sort of fall, the femoral component 18 may become dislodged such that the femoral flange 23 locks onto the overhang 19 of the acetabular component 11. This prevents the femoral vertex from coming loose from the cavity 13 and accordingly it only takes the movement of the leg to its more normal position to reestablish the femoral vertex in the cavity 14. In the embodiment shown in FIG. 5, it is arranged that the length of the cone portion of the femoral component 18 exceeds in length the distance between the acetabular contact point 13 and the overhang 19 such that the situation shown in FIG. 5 will only occur in exceptional circumstances.

Figure 7:
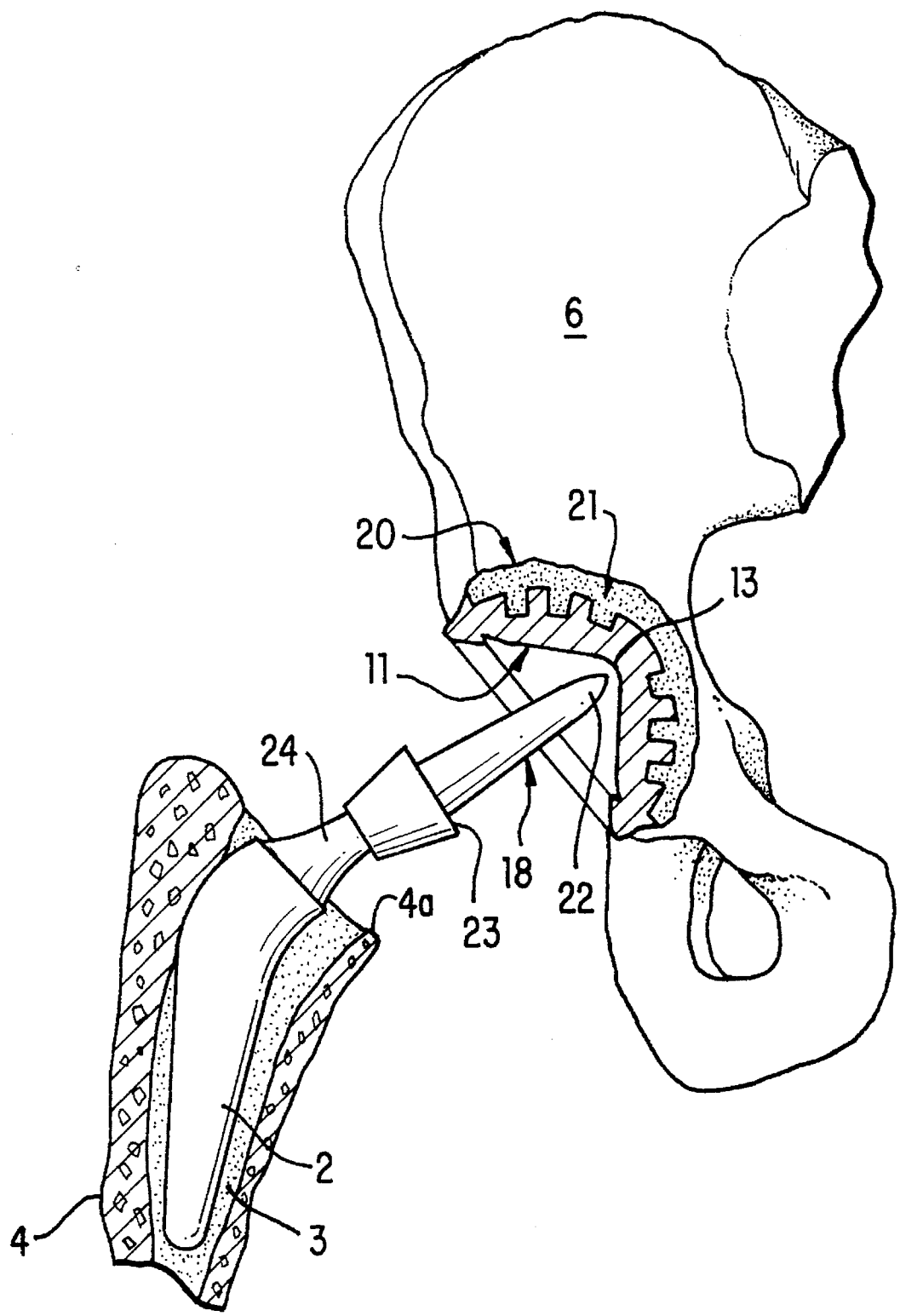
FIG. 7 shows a skeletal view similar to that of FIG. 1 but showing the arrangements of the present invention.
Figure 8A:
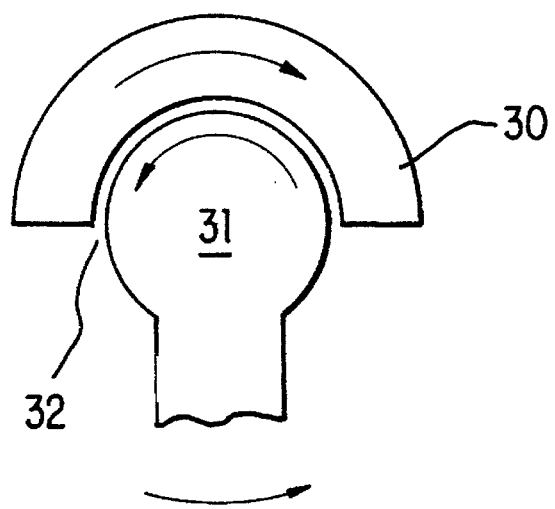
FIG. 8 shows in diagrammatic form the main difference between the prior art (a) and the invention (b).
Figure 8B:
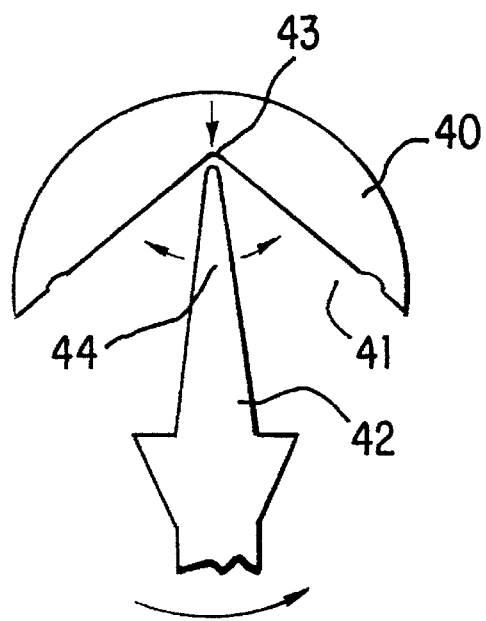

The positioning of the embodiment of this invention is shown best in FIG. 7. In FIG. 7 the iliac bone 6 is provided with an iliac cavity 20 in the normal way. In the iliac cavity 20 is positioned a layer of an acrylic cement 21 and in this is seated an acetabular component 11 in accordance with normal procedures. The acetabular component 11 is formed of cobalt/chromium alloy or other very hard stainless biologically compatible material.

Similarly, the femur 4 is provided with a femur cavity 4A into which is positioned a femoral stem 2 in a layer of an acrylic cement 3. This is arranged such that the femoral neck 24 protrudes from the femur 4. The femoral component 18 which may be integral with the neck 24 or formed separately therefrom and slid into an interengagement protrudes from the femoral neck 24 towards the contact point 13 of the acetabular component.

As will be seen, the vertex 22 of the femoral component 18 nestles against the vertex 13 of the acetabular component 11. Since the femur is in tension relative to the iliac bone, the whole assembly is retained in the position as shown generally in FIG. 7.

Figure 5:
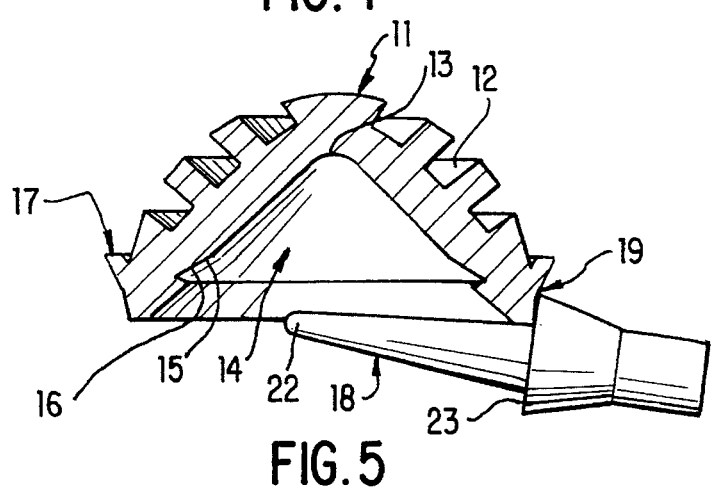

In case the patient were to fall or the legs were to exceed their normal arcuate path especially during the initial period before the capsular scar tissue has retained the articulation in a more secure way, the arrangement of FIGS. 5 and 6 prevents the femoral component 18 from being dislodged from the cavity 14 by the means as shown in FIGS. 5 or 6.

The invention relates therefore to components which together form an arrangement for total hip or any other articulation suitable for arthoplasty. It will thus be appreciated that selected joints in the body may be replaced utilising a similar arrangement to that of a total hip arthroplasty described in the specific embodiment.

I claim:

1. A prosthetic arthoplastic device comprising:

a first component adapted to be affixed in a prepared bone cavity in a first bone structure;

a second component having a first end portion adapted to be affixed in a prepared cavity in a second bone structure which is cooperative with said first bone structure;

the first component having a receiving cavity substantially conically shaped and having a first engagement surface defined by an apex area of said receiving cavity;

said second component having a second engagement surface at a second end thereof for pivotally engaging said first engagement surface; and the second component being free to move through an arc of normal cooperative motion of said first and second bone structures, said arc of motion having an apex maintained within said apex area during a range of said normal operative motion whereby load is transferred from the first component to the second component via the pivotal engagement of said first and second engagement surfaces.

2. A device according to claim 1 wherein the second component is a femoral component and the first component is an acetabular component adapted to be secured in an iliac bone.

3. A device according to claim 1 wherein the second engagement surface is a vertex of a substantially conical portion of said second component which subtends an angle more acute than that of the receiving cavity of said first component.

4. A device according to claim 1 wherein said first and second components are formed of a cobalt/chromium alloy.

5. The device according to claim 1 wherein:

the second engagement surface is a spherical end of a substantially conical portion of said second component; and said substantially conical portion subtends an angle more acute than that of the receiving cavity of said first component.

6. The device according to claim 1 wherein said receiving cavity terminates in a circumferential recess of sufficient depth to entrap the first engagement surface if dislodged from said apex are abnormal conditions.

7. A device according to claim 1 further comprising:

the second component having a flanged portion remote from said second engagement surface;

said first component having an annular rim surrounding said receiving cavity; and the second engagement surface and the flanged portion defining a distance therebetween greater than a distance between the apex area of said receiving cavity and the annular rim thereof.

8. A prosthetic arthoplastic device comprising:

an acetabular component adapted for affixation in a cavity in an iliac bone;

a femoral component adapted to be affixed in a prepared cavity in a femoral bone;

said femoral component having a femoral vertex formed at a distal end thereof for engaging said acetabular component;

said acetabular component having a receiving cavity for accepting the femoral vertex;

said receiving cavity having a substantially conical shape with a cone apex for accepting said femoral vertex;

said substantially conical shape subtending an angle sufficient to permit pivoting of said femoral component about said cone apex through a range providing for femoral motion; and said substantially conical shape terminating in a circumferential recess of sufficient depth to entrap the femoral vertex if dislodged from said cone apex under abnormal conditions.

9. A device according to claim 8 further comprising: the femoral component having a flanged portion remote from said femoral vertex;

said acetabular component having an annular rim surrounding said receiving cavity; and the femoral vertex and the flanged portion defining a distance therebetween greater than a distance between the acetabular apex and the annular rim.

* * * * *